United States Patent [19]

Kohji et al.

[11] Patent Number: 5,494,662
[45] Date of Patent: Feb. 27, 1996

[54] STIMULATOR FOR BONE FORMATION

[75] Inventors: Ueno Kohji; Teruaki Katayama; Tsumoru Miyamoto, all of Osaka, Japan

[73] Assignee: Ono Pharmaceutical Co., Ltd., Osada, Japan

[21] Appl. No.: 49,503

[22] Filed: Apr. 21, 1993

[30] Foreign Application Priority Data

Apr. 27, 1992 [JP] Japan ................................ 4-134194

[51] Int. Cl.⁶ ........................... A61K 48/00; C07K 2/00; C07K 4/00
[52] U.S. Cl. ............................... 424/85.2; 514/7; 514/21

[56] References Cited

FOREIGN PATENT DOCUMENTS

| | | |
|---|---|---|
| 0301835 | 2/1989 | European Pat. Off. . |
| 0302429 | 2/1989 | European Pat. Off. . |
| 0342892 | 11/1989 | European Pat. Off. . |
| 8702990 | 5/1987 | WIPO . |
| 8804667 | 6/1988 | WIPO . |

OTHER PUBLICATIONS

Y. Noma et al, *Nature*, 319, 640 (1986).
E. Severinson et al, *Eur. J. Immunol.*, 17, 67 (1987).
T. R. Mosmann et al, *Proc. Natl. Acad. Sci. USA*, 83, 5654 (1986).
T. Yokota et al, *Proc. Natl. Acad. Sci. USA*, 83, 5894 (1986).
P. H. Hart et al, *Proc. Natl. Acad. Sci. USA*, 86, 3803 (1989).
M. Hurme et al, *Biochem. Biophys. Res. Commun.*, 157, 861 (1988).
K. Watanabe et al, *Biochem. Biophys. Res. Commun.*, 172, 1035 (1990).
Ueno et al., Biochem. Biophys. Res. Comm., vol. 189, pp. 1521–1526, 1992.

*Primary Examiner*—Jill Warden
*Assistant Examiner*—O. Lynn Touzeau
*Attorney, Agent, or Firm*—Stevens, Davis, Miller & Mosher

[57] ABSTRACT

A stimulator for bone formation containing human interleukin 4 or an analogue thereof as an active ingredient. This stimulator is useful for the prevention and treatment of, for example, osteoporosis, osteogenesis imperfecta, injured bone and abnormality of dental and the improvement of metabolic abnormality of bone.

6 Claims, 5 Drawing Sheets

FIGURE 5

His-Lys-Cys-Asp-Ile-Thr-Leu-Gln-Glu-Ile-
Ile-Lys-Thr-Leu-Asn-Ser-Leu-Thr-Glu-Gln-
Lys-Thr-Leu-Cys-Thr-Glu-Leu-Thr-Val-Thr-
Asp-Ils-Phe-Ala-Ala-Ser-Lys-Asn-Thr-Thr-
Glu-Lys-Glu-Thr-Phe-Cys-Arg-Ala-Ala-Thr-
Val-Leu-Arg-Gln-Phe-Tyr-Ser-His-His-Glu-
Lys-Asp-Thr-Arg-Cys-Leu-Gly-Ala-Thr-Ala-
Gln-Gln-Phe-His-Arg-His-Lys-Gln-Leu-Ile-
Arg-Phe-Leu-Lys-Arg-Leu-Asp-Arg-Asn-Leu-
Trp-Gly-Leu-Ala-Gly-Leu-Asn-Ser-Cys-Pro-
Val-Lys-Glu-Ala-Asn-Gln-Ser-Thr-Leu-Glu-
Asn-Phe-Leu-Glu-Arg-Leu-Lys-Thr-Ile-Met-
Arg-Glu-Lys-Tyr-Ser-Lys-Cys-Ser-Ser.

STIMULATOR FOR BONE FORMATION

SUMMARY

This invention is related to a stimulator for bone formation containing human interleukin 4 or an analogue thereof as an active ingredient.

BACKGROUND OF THE INVENTION

It once seemed as if bone growth was stopped after the bone was fully grown, but this is never true. In a body, bones always repeat formation and resorption (metabolism) and thereby a dynamic balance is maintained. At the cell level, osteoblasts which originate from osteoprogenitor cells play an important role in bone formation, and osteoclasts which originate from hematopoietic stem cells play an important role in bone resorption. A circle of bone formation stage→ pause of bone formation→bone resorption stage→bone formation stage, is called remodeling.

The bone formation stage includes:
1st step: differentiation and proliferation of osteoblasts;
2nd step: activation of osteoblasts; and
3rd step: calcification of bone matrix.

In the 1st step, osteoprogenitor cells in marrow are differentiated into osteoblasts and proliferated. In the 2nd step, type I collagen was secreted from activated osteoblasts to form a matrix which is supportive tissues to deposit calcium and phosphorus. Successively, non-collagenous proteins, e.g., osteocalcin and osteonectin etc. are secreted from osteoblasts and are deposited to form bone matrix. In the 3rd step, calcification is carried out by depositing hydroxyapatite crystals $[Ca_{10}(PO_4)_6(OH)_2]$ to the bone matrix.

Osteoblasts have a high alkaline phosphatase activity and contain acidic phospholipids in a high concentration. It is considered that the apatite crystals are produced by their actions.

On the other hand, the bone resorption stage divided into:
1st step: degradation of uncalcified bone matrix (osteoid);
2nd step: induction of the formation of osteoclasts; and
3rd step: activation of osteoclasts.

The surface of bone is covered with an osteoid consisting of type I collagen as a main component. Osteoid is digestively resorbed by collagenase secreted from osteoblasts (1st step). Migration of osteoclasts to the bone is induced by the action of degradation products of collagenase produced at the former step. Osteoclasts are adhered via adhesion molecules (vitronectin) (2nd step). Carbonate dehydrogenase is produced by the action of activated osteoclasts, and calcium phosphate is dissolved out by the enzyme, and further catepcin L secreted from osteoclasts degradate bone matrix (3rd step).

Interleukin-4 (abbreviated as IL-4 hereafter) is a glycoprotein which T lymphocytes produce when they are stimulated with lectin, phorbol ester or antigen. IL-4 has been identified as a factor in a body, relating to differentiation and proliferation of B lymphocytes or T lymphocytes [see Y. Noma et al., Nature, 319, 640(1986); F. Lee et al., Proc. Natl. Acad. Sci. USA, 83, 2061(1986); E. Severinson et al., Eur. J. Immunol., 17, 67(1987) and T. R. Mosmann et al., Proc. Natl. Acad. Sci. USA, 83, 5654(1986), the disclosures of all of which are incorporated herein by reference].

In 1986, c-DNA of human IL-4 was cloned, thereby revealing that IL-4 is a substance having a molecular weight of 18–21 Kd, consisting of 153 amino acid [see T. Yokota et al., Proc. Natl. Acad. Sci. USA, 83, 5894(1986), the disclosures of all of which are incorporated herein by reference].

In the 153 amino acids, 24 amino acids at the N-terminal form a signal peptide. Therefore, the mature IL-4 has the remaining 129 amino acids (molecular weight of 15 Kd) as a core peptide, attaching sugar chains, and being of a molecular weight of 18–21 Kd as a whole.

According to recent investigation it has been found that IL-4 has biological activities relating to not only B lymphocytes and T lymphocytes but also hematocytes. In particular, it has been found that IL-4 suppressively acts on macrophages and inhibits the release of various kinds of cytokines such as interleukin-1 (IL-1), tumor necrosis factor (TNF), interferon (IFN) etc., derived from macrophages [see P. H. Hart et al., Proc. Natl. Acad. Sci. USA, 86, 3803(1989) and M. Hurme et al., Biochem. Biophys. Res. Commun., 157, 861(1988), the disclosures of all of which are incorporated herein by reference].

More recently, it has been reported that IL-4 inhibited bone resorption stimulated by parathyroid hormone etc. [K. Watanabe et al., Biochem. Biophys. Res. Commun., 172(3), 1035(1990), the disclosures of all of which is incorporated by reference]. It is described therein that the authors conducted their experiment, taking into consideration that IL-4 inhibits the differentiation of hematopoietic stem cells to osteoclasts and the proliferation of osteoclasts and thereby induced the inhibition of bone resorption, because osteoclasts are derived from hematopoietic stem cells as a precursor in common with monocytes/macrophages on which IL-4 may exert effects. The results as expected were given.

On the other hand, it is necessary to provide large amounts of IL-4 for clinical use. Many methods have been developed for transforming a gene of IL-4 into genes of yeast, E. coli, or various mammalian cells and culturing the transformants to produce large amount of the desired IL-4. They are described in detail, for example, in the specifications of the European Patent Publication No. 302429, PCT Publication No. WO 87/02990, and European Patent Publication No. 301835 and 342892, the disclosures of all of which are incorporated by reference herein. Each IL-4 obtained by various methods has fundamentally the same core peptide as natural IL-4 has, in spite of a slight difference, for example, having or not having a sugar chain. Therefore, they are proved to have the same biological activities as natural IL-4 has. Recently, it has been proposed that IL-4 analogues in which a part of the amino acids composing core peptides of human IL-4 be removed or exchanged, or in which other amino acids or other polypeptide be added to core peptides. For example, it is described in the specification of the PCT Publication No. WO 88/04667, the disclosures of all of which is incorporated herein by reference, that IL-4 analogues subjected to the addition or exchange to the core peptides have the same biological activity as natural IL-4 has.

Purpose of the Invention

As the result of investigations of the action of IL-4 on osteoblasts from the above viewpoints, the present inventors have unexpectedly found that IL-4 has a stimulatory activity on the activation of osteoblasts and the calcification of bone matrix, and have accomplished the present invention.

The action of IL-4 on osteoblasts is quite unknown, and further it is not easy to predict that IL-4 has a stimulatory activity on osteoblasts from the literature above described (i.e. Biochem. Biophys. Res. Commun.). Because osteoblasts are differentiated from osteoprogenitor cells which are quite different from the precursor of osteoclasts, which are common precursors with monocytes/macrophages on which IL-4 is known to exert effects.

BRIEF DESCRIPTION OF THE DRAWINGS

FIG. 5 is an illustration of the amino acid sequence of native human IL-4.

DISCLOSE OF THE INVENTION

Figure 1:
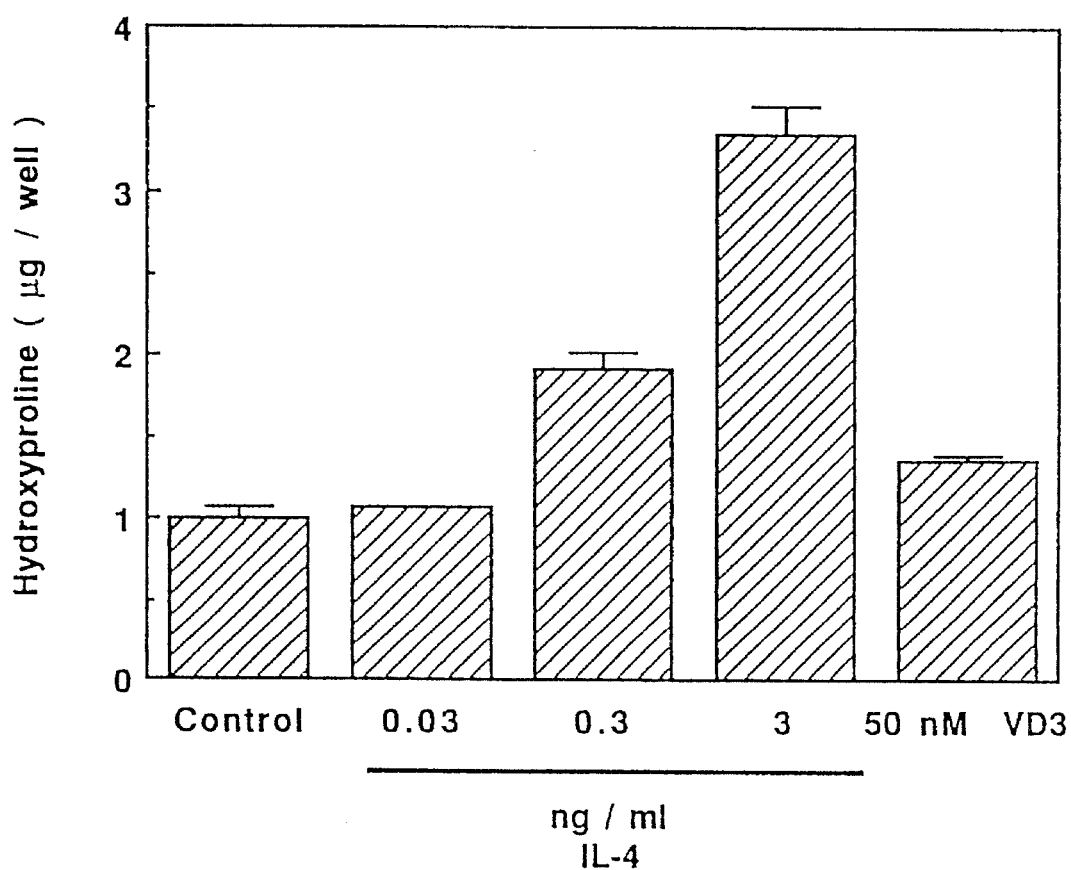
FIG. 1 shows an effect of human IL-4 on the production of hydroxyproline.

The present invention relates to a stimulator for bone formation containing human IL-4 or an analogue thereof as an active ingredient.

In the present invention, human IL-4 and its analogues contained as an active ingredient include natural human IL-4 and substances whose structure has a polypeptide of the same amino acids sequence as natural human IL-4, as a core peptide, optionally subjecting amino acids in the core peptide to chemical modification such as sugar addition, phosphorylation, nucleic acid addition, lipid addition, and which has the same biological activities as human IL-4 described above. Further, analogues of human IL-4 include substances whose structure has, as a core peptide, polypeptides modified by the removal of a part of the amino acids in the core peptide, or by the replacement of it with other amino acids or the addition of one or more amino acids in the core peptide, optionally subjecting to the chemical modification hereinbefore described, and which has the same biological activity as human IL-4. SEQ. ID NO. 1

A preferred embodiment of the invention is the set of glycosylated or unglycosylated human IL-4 proteins and muteins defined by the following formula:

| | | | | | |
|---|---|---|---|---|---|
| X(His)— | X(Lys)— | X(Cys)— | X(Asp)— | X(Ile)— | X(Thr)— |
| X(Leu)— | X(Gln)— | X(Glu)— | X(Ile)— | X(Ile)— | X(Lys)— |
| X(Thr)— | X(Leu)— | X(Asn)— | X(Ser)— | X(Leu)— | X(Thr)— |
| X(Glu)— | X(Gln)— | X(Lys)— | X(Thr)— | X(Leu)— | X(Cys)— |
| X(Thr)— | X(Glu)— | X(Leu)— | X(Thr)— | X(Val)— | X(Thr)— |
| X(Asp)— | X(Ile)— | X(Phe)— | X(Ala)— | X(Ala)— | X(Ser)— |
| X(Lys)— | X(Asn)— | X(Thr)— | X(Thr)— | X(Gln)— | X(Lys)— |
| X(Glu)— | X(Thr)— | X(Phe)— | X(Cys)— | X(Arg)— | X(Ala)— |
| X(Ala)— | X(Thr)— | X(Val)— | X(Leu)— | X(Arg)— | X(Gln)— |
| X(Phe)— | X(Tyr)— | X(Ser)— | X(His)— | X(His)— | X(Glu)— |
| X(Lys)— | X(Asp)— | X(Thr)— | X(Arg)— | X(Cys)— | X(Leu)— |
| X(Gly)— | X(Ala)— | X(Thr)— | X(Ala)— | X(Gln)— | X(Gln)— |
| X(Phe)— | X(His)— | X(Arg)— | X(His)— | X(Lys)— | X(Gln)— |
| X(Leu)— | X(Ile)— | X(Arg)— | X(Phe)— | X(Leu)— | X(Lys)— |
| X(Arg)— | X(Leu)— | X(Asp)— | X(Arg)— | X(Asn)— | X(Leu)— |
| X(Trp)— | X(Gly)— | X(Leu)— | X(Ala)— | X(Gly)— | X(Leu)— |
| X(Asn)— | X(Ser)— | X(Cys)— | X(Pro)— | X(Val)— | X(Lys)— |
| X(Glu)— | X(Ala)— | X(Asn)— | X(Gln)— | X(Ser)— | X(Thr)— |
| X(Leu)— | X(Glu)— | X(Asn)— | X(Phe)— | X(Leu)— | X(Glu)— |
| X(Arg)— | X(Leu)— | X(Lys)— | X(Thr)— | X(Ile)— | X(Met)— |
| X(Arg)— | X(Glu)— | X(Lys)— | X(Tyr)— | X(Ser)— | X(Lys)— |
| X(Cys)— | X(Ser)— | X(Ser)— | | | | wherein the term X(Xaa) represents the group of synonymous amino acids to the amino acid Xaa. Synonymous amino acids within a group have sufficiently similar physicochemical properties for substitution between members of the group to preserve the biological function of the molecule: Grantham, *Science*, Vol. 185, pp. 862–864 (1974). It is clear that insertions and deletions of amino acids may also be made in the above-defined sequence without altering biological function, particularly if the insertions or deletions only involve a few amino acids, e.g., under ten, and do not remove or displace amino acids which are critical to a functional conformation, e.g., cysteine residues, Anfisen, "Principles That Govern the Folding of Protein Chains", *Science*, Vol. 181, pp. 223–230 (1973). Proteins and muteins produced by such deletions and/or insertions come within the purview of the present invention. Whenever amino acid residues of the protein of Formula I are referred to herein by number, such number or numbers are in reference to the N-terminus of the protein.

Preferably the synonymous amino acid groups are those defined in Table I. More preferably, the synonymous amino acid groups are those listed before the second slash in each line in Table I.

TABLE I

| Preferred Groups of Synonymous Amino Acids | |
|---|---|
| Amino Acid | Synonymous Group |
| Ser | Ser,//Thr, Gly, Asn |
| Arg | Arg,/His, Lys,/Glu, Gln |
| Leu | Leu, Ile, Met,/Phe,/Val, Tyr |
| Pro | Pro,/Ala,/Thr, Gly |
| Thr | Thr,//Pro, Ser, Ala, Gly, His, Gln |
| Ala | Ala,/Pro,/Gly, Thr |
| Val | Val,/Met, Ile/Tyr, Phe, Leu, Val |
| Gly | Gly,//Ala, Thr, Pro, Ser |
| Ile | Ile, Met, Leu,/Phe, Val,/Ile, Tyr |
| Phe | Phe,/Met, Tyr, Ile, Leu,/Trp, Val |
| Tyr | Tyr,/Phe,/Trp, Met, Ile, Val, Leu, |
| Cys | Cys, Ser,//Thr |
| His | His,/Gln, Arg,/Lys, Glu, Thr |
| Gln | Gln,/Glu, His,/Lys, Asn, Thr, Arg |
| Asn | Asn,/Asp,/Ser, Gln |
| Lys | Lys,/Arg,/Glu, Gln, His |
| Asp | Asp,/Asn,/Glu |
| Glu | Glu,/Gln,/ Asp, Lys, Asn, His, Arg |
| Met | Met, Ile, Leu,/Phe, Val/ |

The invention includes the polypeptides of Formula I with amino acid substitutions (between an amino acid of the native human IL-4 and a synonymous amino acid) at a single position or at multiple positions. The term "N-fold substituted" is used to describe a subset of polypeptides defined by Formula I wherein the native amino acids have been substituted by synonymous amino acids at at least N positions. Thus, for example, the group if 1-fold substituted polypeptide of Formula I consists of 559 polypeptides for the preferred groups of synonymous amino acids, 189 for the more preferred groups of synonymous amino acids, and 56 for the most preferred groups of synonymous amino acids. These numbers were arrived at by summing the number of amino acids of each kind in the native chain times the size of the synonymous amino acid group for that amino acid. Preferably the group of human IL-4 polypeptides consists of the 10-fold substituted polypeptides of Formula I; more preferably it consists of 3-fold substituted polypeptides of Formula I; and most preferably it consists of 1-fold substituted polypeptides of Formula I, which in particular includes the native human IL-4 polypeptide whose sequence is illustrated in FIG. 5.

Likewise, the term "N-fold inserted" in reference to the peptides of Formula I is used to describe a set of polypeptides wherein from 1 to N amino acids have been inserted into the sequence defined by Formula I. Preferably, the inserted amino acids are selected from the preferred groups of synonymous amino acids (Table I) of the amino acids flanking the insertion. Thus, for example, one subgroup of the group of 1-fold inserted peptides comprises an amino acid inserted between the N-terminal X(His) and the adjacent X(Gly). The insertions defining the members of this subgroup are preferably selected from the group consisting of Pro, Ala, Gly, Thr, Ser, Gln, Glu, Arg, His, and Lys; more preferably they are selected from the group consisting of Gly, His, Gln and Arg, and most preferably they are selected from the group consisting of His and Gly. Insertions can be made between any adjacent amino acids of Formula I. Since there are 128 possible insertion locations, and since multiple insertions can be made at the same location, a 2-fold inserted peptide of Formula I gives rise to 16,384 subgroups of peptides, and the size of each subgroup depends on the sizes of the synonymous amino acid groups of the amino acids flanking the insertions.

The term "N-fold deleted" in reference to the polypeptides of Formula I is used to describe a set of peptides having from 1 to N amino acids deleted from the sequence defined by Formula I. Thus, the set of 1-fold deleted polypeptides of Formula I consists of 129 subgroups of polypeptides each 128 amino acids in length (128-mers). Each of the subgroups in turn consists of all the 128-mers defined by the preferred, more preferred, and most preferred synonymous amino acid groups.

The invention further includes nucleotide sequences effectively homologous to or capable of encoding the polypeptides of Formula I for the preferred, more preferred, and most preferred groups of synonymous amino acids. More preferably said nucleotide sequences are capable of encoding the polypeptides of Formula I for the preferred, more preferred, and most preferred groups of synonymous amino acids.

Shortle, in *Science*, Vol. 229, pp. 1193–1201 (1985), reviews techniques for mutating nucleic acids which are applicable to the present invention. Preferably, mutants of the native IL-4s, i.e., IL-4 muteins, are produced by site-specific oligonucleotide-directed mutagenesis, e.g., Zollar and Smith, *Methods in Enzymology*, Vol. 100, pp. 468–500 (1983); Mark et al, U.S. Pat. No. 4,518,584 entitled "Human Recombinant Interleukin-2 Muteins"; or by so-called "cassette" mutagenesis described by Wells et al, in *Gene*, Vol. 34, pp. 315–323 (1985); and Estell et al, *Science*, Vol. 233, pp. 659–663 (1986). In seconds below, the notation used by Estell et al (cited above) to identify muteins is followed and generalized. For example, "human IL-4 mutein Leu$^{82}$" (or simply "Leu$^{82}$" if the native protein is understood from the context) indicates a polypeptide whose amino acid sequence is identical to that of the native protein except for position 82 with respect to the N-terminus. At that position Leu has been substituted for Phe. More than one substitution can be similarly indicated; e.g., a mutein having Leu substituted for Phe at position 82 and Asp for Asn at position 111 is referred to as human IL-4 mutein (Leu$^{82}$, Asp$^{111}$). Deletions are indicated by Δ's". For example, a mutein lacking Gln at position 71 is referred to as human IL-4 mutein Δ$^{71}$. An insertion is indicated by "IS(Xaa)". For example, a mutein with a Leu inserted after Gln at position 71 is referred to as human IL-4 as human IL-4 mutein IS$^{71}$(Leu). Thus, human IL-4 mutein (Ser$^{13}$, Δ$^{71}$, IS$^{94}$(Gly)) represents the native human IL-4 sequence which has been modified by replating Thr by Ser at position 13, deleting Gln at position 71, and inserting Gly immediately after Ala at position 94. Insertion of multiple amino acids at the same site is indicated by IS$^i$(Xaa$_1$-Xaa$_2$-Xaa$_3$- . . . ), where Xaa$_1$-Xaa$_2$-Xaa$_3$ . . . is the sequence inserted after position i. N-terminal additions are indicated by superscript "O", e.g, IS$^O$(Xaa), and a sequence of deletions, for example, of amino acids 6–10, is designated either as Δ$^{6-10}$, or as (Δ$^6$, Δ$^7$, Δ$^8$, Δ$^9$, Δ$^{10}$).

Most preferably cassette mutagenesis is employed to generate human IL-4 muteins. As described more fully below, a synthetic human IL-4 gene has been constructed with a sequence of unique restriction endonuclease sites spaced approximately uniformly along the gene. The uniqueness of the restriction sites should be retained when the gene is inserted into an appropriate vector, so that segments of the gene can be conveniently excised and replaced with synthetic oligonucleotides (i.e., "cassettes") which code for desired muteins.

The present invention includes glycosylated or unglycosylated mammalian polypeptides which exhibit IL-4 activity, and which are derivable from the IL-4 polypeptides disclosed herein using standard protein engineering techniques. The invention also includes nucleic acids having sequences capable of coding for the polypeptides of the invention, and nucleic acids whose sequences are effectively homologous to the cDNA clones of the invention. Finally, the invention includes methods of making the glycosylated or unglycosylated polypeptides of the invention which utilize the nucleotides sequences disclosed herein, and methods of using the polypeptides of the invention.

Natural human IL-4 may be obtained by culturing cells producing IL-4 (e.g. spleen cells etc.) with a stimulator, and by recovering human IL-4 in the medium, and then purifying.

Human IL-4 analogues include recombinant human IL-4 (abbreviated as rhIL-4 hereafter) largely produced by genetic engineering techniques. rhIL- 4 is known to be prepared by using not only mammalian cells such as COS-7 cells and CHO cells but also *E. coli* and yeast, as host cells, but not limited to them. For example, rhIL-4 produced by CHO cells is described in detail in the specification of the European Patent Publication No. 302429, the disclosure of which is hereby incorporated by reference. rhIL-4 produced by COS-7 cells, *E. coli* and yeast, is described in detail in the specification of the PCT Publication No. WO 87/02990 and European Patent Publication No. 301835 and 342892, the disclosure of which are hereby incorporated by reference. It is confirmed that all of them has the same biological activity as natural human IL-4 has.

rhIL-4 wherein the core peptide itself is modified, is described in the specification of the PCT Publication No. WO 88/04667, the disclosure of which is hereby incorporated by reference. In this paper, rhIL-4 (Asp$^{62}$, Asp$^{129}$) and Glu Ala Glu Ala-hIL-4 (Asp$^{62}$, Asp$^{129}$) are specifically prepared, and both are confirmed to have the same biological activity as human IL-4 has.

Effect of the Invention

Human IL-4 and its analogues used in the present invention possess strong stimulatory activity on the activation of human osteoblasts and the calcification of bone matrix and, therefore, may be useful as stimulators for bone formation, and for the prevention and the treatment of various bone diseases, for example, (1) the prevention and treatment of osteoporosis which is caused by aging or pharmaceuticals etc.,
(2) the prevention and treatment of osteogenesis imperfecta,
(3) the treatment of injured bones such as fractures etc.,
(4) the prevention and treatment of abnormality in the dental area, and
(5) the improvement of metabolic abnormality of bone which is derived from the disease of articular rheumatism etc.

The toxicity of human IL-4 and its analogues used in the present invention is very low, and therefore, it may be considered that they are fully safe for pharmaceutical use. For example, no female "Macaca Fuscata" were dead by administration of rhIL-4 originated from CHO cells at the dose of 1 mg/kg (intravenously), 2 mg/kg (i.v. infusion for 20 min.) and daily injection at 500 µg/kg (intravenously) for 7 days. Further, no change was found in blood pressure, electrocardiogram, heart rate, respiration rate and temperature. Furthermore, it is considered that there is no problem of toxicity for humans because human IL-4 is an essential secretory protein in the body.

Application for Pharmaceuticals

For the purpose above described, human IL-4 and its analogues may be normally administered systematically or partially, usually by oral or parenteral administration (preferable intravenous).

The doses to be administered are determined depending upon age, body weight, symptom, the desired therapeutic effect, the route of administration, and the duration of the treatment etc. In the human adult, the doses per person per dose are generally between 1 mg and 10 mg, by oral administration, up to several times per day, and between 10 µg and 1 mg, by parenteral administration (preferable intravenous) up to several times per day.

As mentioned above, the doses to be used depend upon various conditions. Therefore, there are cases in which doses lower than or greater than the ranges specified above may be used.

The administration of the compounds of the present invention can be as a solid composition, liquid compositions or other compositions for oral administration, and as injections, liniments or suppositories etc. for parenteral administration.

Solid compositions for oral administration include compressed tablets, pills, capsules, dispersible powders, and granules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), assisting agents for dissolving (such as arginine, glutamic acid, asparaginic acid etc.), and stabilizing agents (such as human serum albumin, lactose, etc.).

The tablets or pills may, if desired, be coated with a film of gastric or enteric material (such as sugar, gelatin, hydroxypropyl cellulose or hydroxypropylmethyl cellulose phthalate, etc.).

Capsules include hard capsules and soft capsules.

Liquid compositions for oral administration include pharmaceutically-acceptable solutions, emulsions, suspensions, syrups and elixirs. In such compositions, one or more of the active compound(s) is or are contained in inert diluent(s) commonly used in the art (Purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer(sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. In such compositions, one more of active compounds(s) is or are admixed with at least one of inert aqueous diluent(s) (distilled water for injection, physiological salt solution etc.) and inert non-aqueous diluent(s) (propylene glycol, polyethylene glycol, olive oil, ethanol, POLYSORBATE80 (registered trade mark), etc.).

Injections may comprise additional agents other than inert diluents: e.g. preserving agents, wetting agents, emulsifying agents, dispersing agents, stabilizing agent (human serum albumin, lactose, etc.), assisting agents such as assisting agents for dissolving (arginine, glutamic acid, asparaginic acid, polyvinylpyroridone etc.).

They may be sterilized for example, by filtration through a bacteriaretaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

EXAMPLE

The following examples are illustrative but do not limit the present invention.

Example 1

Stimulatory effect of human IL-4 on the activation of human osteoblasts and the calcification of bone matrix.

(1) Method

Human osteoblasts derived from the ulnar periosteum in a man of 20 years of age (prepared by the method described in Biochem. Biophys. Res. Commun., 145, 651 (1987), the disclosure of which is incorporated herein) were cultured in α-MEM (alpha modification of Eagles' minimal essential medium) containing 10% fetal bovine serum in an incubator at 37° C. in 5% $CO_2$ gas - 95% air. The medium was changed every other day. After the cells had reached confluence, the cells were dispersed by a mixture of 0.025% trypsin and 0.05% EDTA. After being suspended homogeneously, the suspension was recultured on new culture dishes in a split ratio of 1:2 or 1:4 and subcultivation was carried out. Human osteoblasts (19PDL) thus obtained were cultured on a 24-multiwell plate ($3.3 \times 10^4$ cells/well). After the plate was filled with cells (state of confluent), human IL-4 (rhIL-4 prepared by the method described in the specification of the European Patent Publication No. 302429, the disclosure of which is incorporated herein by reference) was added to the medium at the prescribed concentration (0.03, 0.3 or 3 ng/ml as final concentration) and the cells were cultured for an additional 20–24 days in the presence of 2 mM of sodium salt of α-glycerophospholic acid. During this period, the medium containing human IL-4 was replaced every other day. In this experiment, 1, 25-dihydroxyvitamin $D_3$ (abbreviated as $VD_3$ hereinafter) was used as the positive control.

After the cells were cultured, the amounts of collagen, osteocalcin, calcium and phosphorus in the extracellular matrix were measured.

After the medium was removed from the culture plate, the plate was washed twice with Hanks' balanced salt solution (pH 7.4). Cells were collected and the hydroxyproline content of the extracellular matrix was measured according to the method of Blumenkrantz et al. (the method described in Anal. Biochem., 55, 288 (1973), the disclosure of which is incorporated herein by reference). Hydroxyproline content is given as an indication of the collagen content produced by the osteoblast.

After the cells were washed twice with Hanks' balanced salt solution (pH 7.4), osteocalcin was extracted with 20% formic acid and was measured using BGP IRMA kit (trade name, being on the market from Mitsubishi Petrochemical Co., Ltd.).

In order to measure calcium and phosphorus, the cells were washed twice with Hanks' balanced salt solution (pH 7.4) and a cold 5% perchloric acid was added thereto, followed by shaking for 15 min. to extract the calcium and phosphorus. The amounts of calcium and phosphorus in the extract were measured using Calcium C-test Wako and P-test Wako (both trade names, being on the market from Wako Pure Chemical Ind., Ltd.), respectively.

(2) Results

Figure 2:
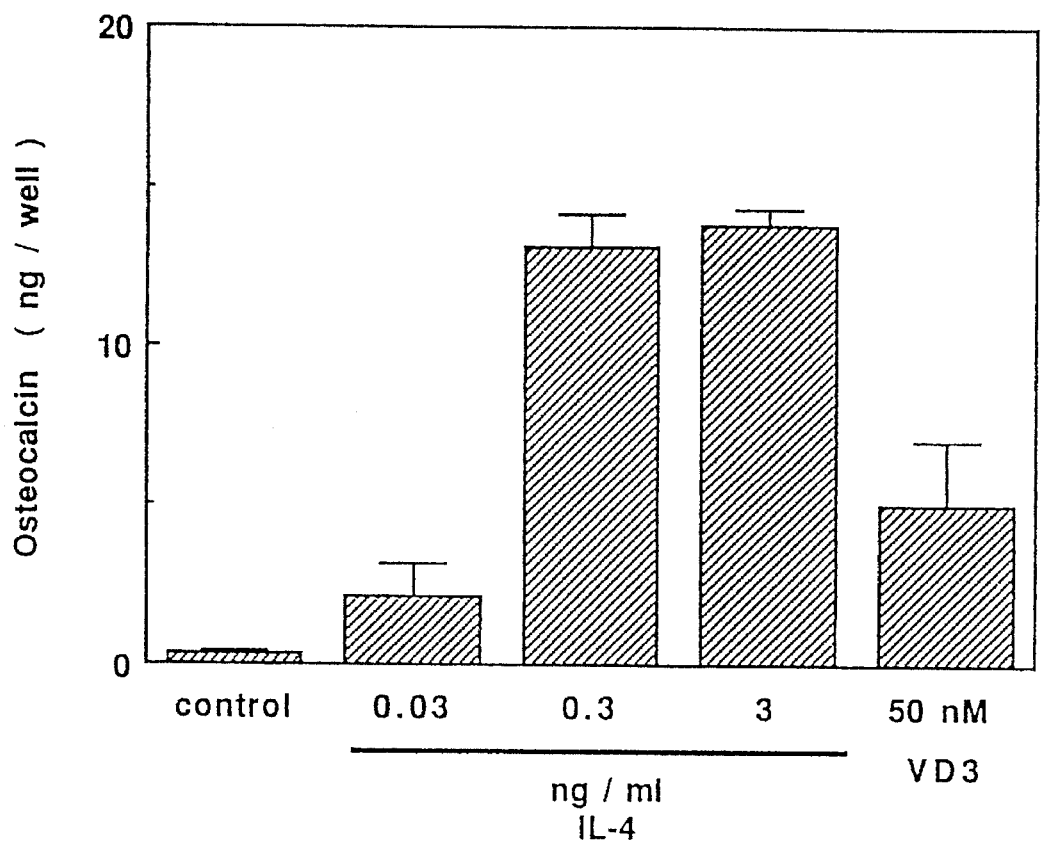
FIG. 2 shows an effect of human IL-4 on the accumulation of osteocalcin.
Figure 3:
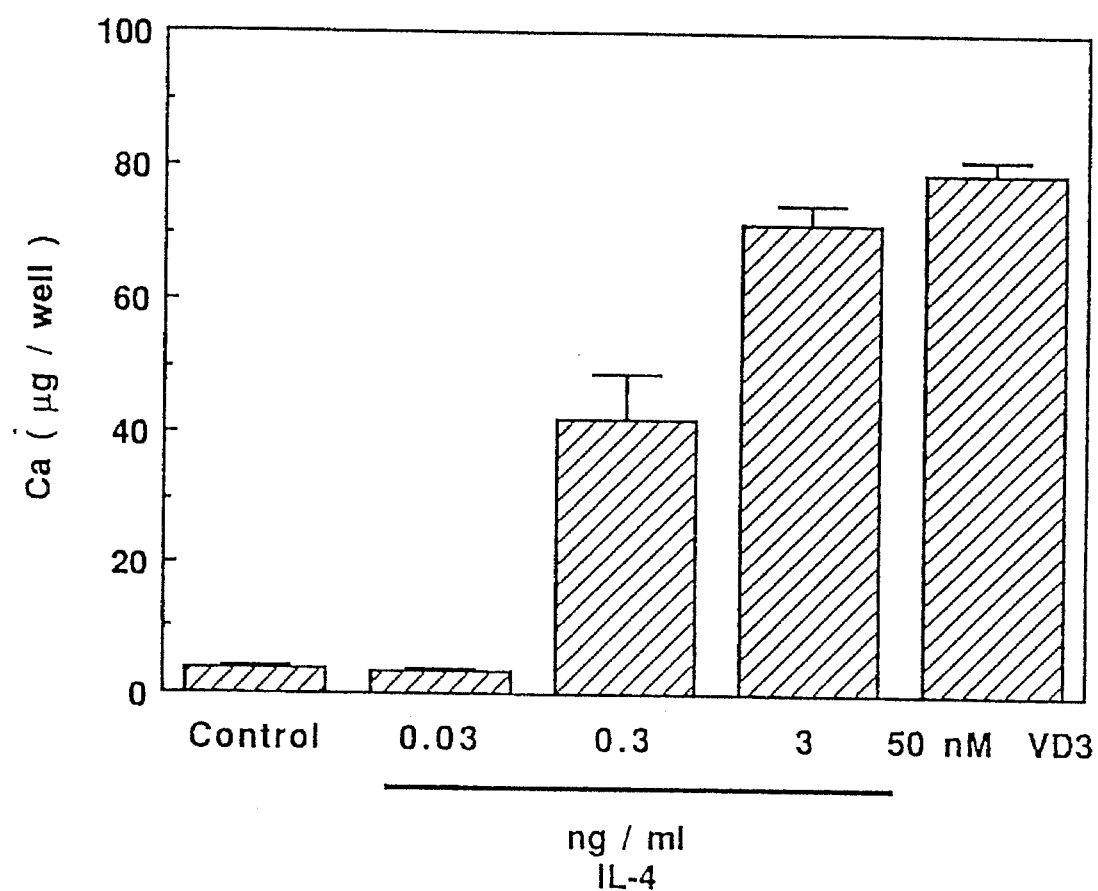
FIG. 3 shows an effect of human IL-4 on the calcium deposition.
Figure 4:
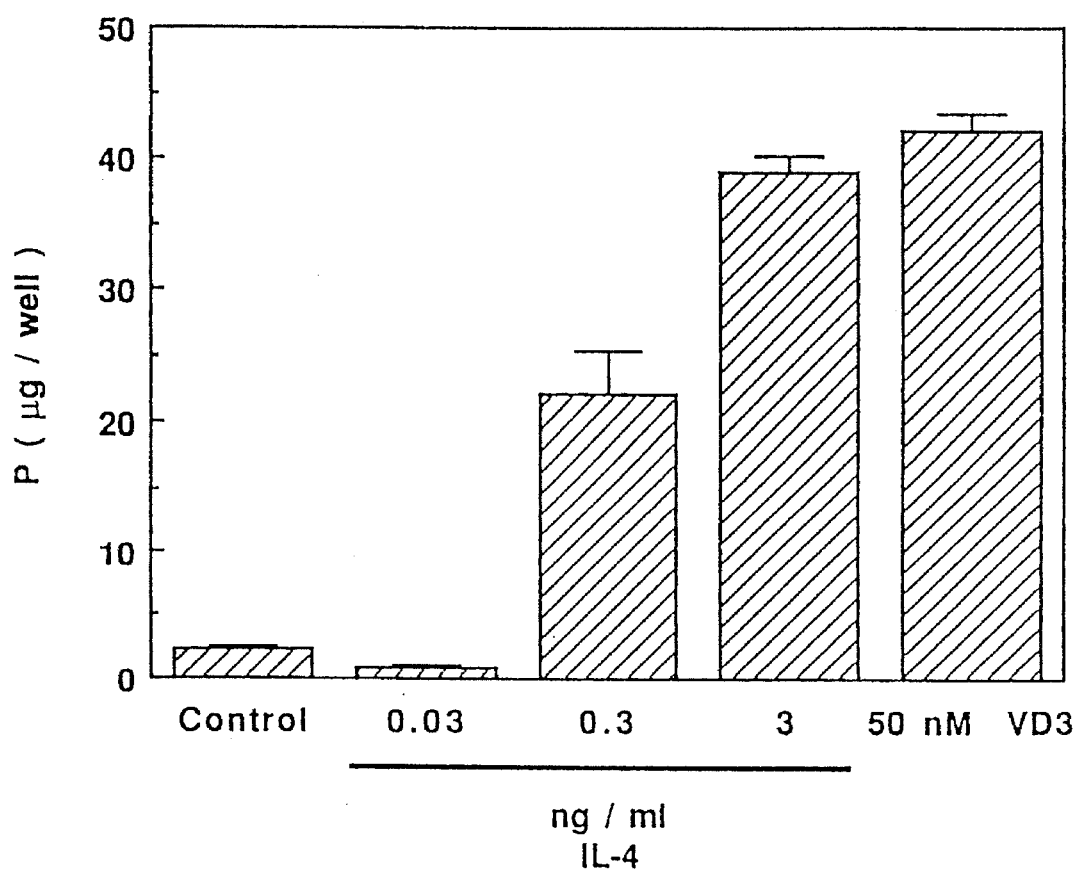
FIG. 4 shows an effect of human IL-4 on the phosphorus deposition.

The results are shown in FIGS. 1 to 4. As can be seen from the figures, the amounts of collagen and osteocalcin produced, and the amount of calcium and phosphorus deposited are increased dose-dependently by IL-4. The fact shows that IL-4 stimulates the activation of osteoblasts and the calcification of bone matrix.

Formulation example

Human IL-4 (10 mg) is fully dissolved into physiological saline (500 ml). The obtained solution is sterilized in a conventional manner, placed in 5 ml portions into ampules and freeze-dried to obtain 100 ampules each containing 100 μg of the active ingredient.

Example 2

Expression of Native Human IL-4 and Mutein IS$^O$ (Ala-Glu-Phe) in *E. coli*

Two vectors containing human IL-4 cDNA inserts were constructed for expression of human IL-4 in *E. coli*: a pIN-III secretion vector which contains the signal peptide sequence of the ompA protein ("pIN-III-ompA2"), and a pUC12 plasmid containing a trpP promoter and an adjacent ribosome binding site (RBS) region ("TRPC11").

A. pIN-III-ompA2

Two vectors were constructed using the pIN-III-ompA2 plasmid, which is described by Ghrayeb et al in *EMBO Journal*, Vol. 3, pp. 2437–2442 (1984), and Masui et al in *Biotechnology*, Vol. 2, pp. 81–85 1984).

The first vector, designated pIN-III-ompA2(1), was constructed by ligating, in series, the EcoRI/BamHI-digested pIN-III-ompA2 plasmid, a synthetic linker, and the BamHI/EcoRV fragment of pcD-125. The synthetic linker used in this construction resulted in the secretion of a biologically active IL-4 polypeptide having the three extra N-terminal amino acids Ala-Glu-Phe; ie., mutein IL$^O$(Ala-Glu-Phe) was secreted. The synthetic linker consisted of the following sequences of nucleotides:

| AA TTC CAC AAG TGC GAT | SEQ. ID NO. 2 |
| G GTG TTC ACG CTA | SEQ. ID NO. 3 |

EcoRI/BamHI-digested pIN-III-ompA2 and the BamHI/EcoRV fragment of pcD-125 were mixed in a standard ligation solution (e.g., Maniatis et al, cited above) containing 0.1 micromolar of the synthetic linker. *E. coli* strain Ab1299 was transfected by the pIN-III-ompA2(1) plasmid and transformants were selected by colony hybridization using a $^{32}$P-labeled IL-4 cDNA probe. Human IL-4 extracts for assaying were obtained as follows. After sonication, the bacterial cultures were centrifuged, and the supernatant removed from the pellet. The pellet was treated with 1% SDS, 2 mM dithiothreitol, and 6 M guanidine. The material was recentrifuged, the supernatant discarded, and the pellet treated at 45° C. with 3% SDS and 2 mM dithiothreitol. The material was again centrifuged, and the supernatant assayed by SDS-PAGE.

pIN-III-ompA(2) was constructed so that the native human IL-4 would be expressed. The three amino acid addition in the pIN-III-ompA(1) construction was eliminated by site-specific mutagenesis of the ompA signal peptide sequence of pIN-III-ompA2. The site-specific mutagenesis was carried out as disclosed by Zoller and Smith (cited above). Briefly, the XbaI/BamHI fragment of pIN-III-ompA2 containing the coding sequence for the ompA signal peptide (see FIG. 1 in Ghrayeb et al, cited above) was purified, mixed with purified XbaI/BamHI-digested replicating form (RF) of M13mp19, ligated, transfected into *E. coli* K-12 JM101, and plated. A clear plaque in the presence of IPTG and X-gal was selected and propagated, and single stranded DNAs were prepared, e.g., according to the procedures disclosed by Messing in *Methods in Enzymology*, Vol. 101 (Academic Press, New York, 1983). Separately, the following oligonucleotide primer (23-mer) containing the indicated based substitutions (boxed) was synthesized and phosphorylated:

5'-GGAATTCAGAAGCT TG C G GCTAC-3'    SEQ. ID NO. 4

This sequence introduces a second HindIII site in the signal peptide coding region of the mutated pIN-III-ompA2. The oligonucleotide primer was annealed to the M13mp19 RF containing the XbaI/BamHI fragment of pIN-III-ompA2, and treated with DNA polymerase in the presence of appropriate concentrations of nucleoside triphosphates. The resulting RFs were used to transfect JM101 *E. coli*, and mutant-containing plaques were screened by a labeled oligonucleotide probe. The sequence of the selected RF was confirmed by dideoxy sequencing using a universal M13 primer. The selected RF was propagated, isolated, and digested with XbaI and BamHI, and the purified XbaI/BamHI fragment was inserted into an XbaI/BamHI-digested pIN-III-ompA2. To form pIN-III-ompA2(2), the mutant pIN-III-ompA2 was propagated, purified, digested with HindIII and BamHI, and mixed with the BamHI/EcoRV fragment of pcD-125 in a standard ligation solution containing 0.1 micromolar of the following synthetic linker:

| A GCT CAC AAG TGC GAT | SEQ. ID NO. 5 |
| GTG TTC ACG CTA | SEQ. ID NO. 6 |

*E. coli* strain Ab1899 was transfected by the pIN-III-ompA2(2) plasmid and transformants were selected by colony hybridization using a $^{32}$P-labeled IL-4 cDNA probe. IL-4 extracts, prepared as described above, exhibited TCGF activity comparable to supernatants of pcD-125 COS7 cells.

B. TRPC11

The TRPC11 vector was constructed by ligating a synthetic consensus RBS fragment to ClaI linkers (ATGCAT) and by cloning the resulting fragments into ClaI-restricted pMT11hc (which had been previously modified to contain the ClaI site). pMT11hc is a small (2.3 kilobase) high copy, $AMP^R$, $TET^S$ derivative of pBR322 that bears the EcoRI-HindIII polylinker region of the πVX plasmid (described by Maniatis et al, cited above). It was modified to contain the ClaI site by restricting pMT11hc with EcoRI and BamHI, filling in the resulting sticky ends and ligating with ClaI linker (CATCGATG), thereby restoring the EcoRI and BamHI sites and replacing the SmaI site with a ClaI site.

One transformant form the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI and treating with T4 DNA polymerase in the presence of all four deoxynucleotide triphosphates. The resulting 30-40 bp fragments were recovered via PAGE and cloned into SmaI-restricted pUC12. A 248 bp E. coli trpP-bearing EcoRI fragment derived from pKC101 (described by Nichols et al in *Methods in Enzymology*, Vol. 101, pg. 155 [Academic Press, N.Y. 1983)] was then cloned into the EcoRI site to complete the TRPC11 construction.

TRPC11 was employed as a vector for human IL-4 cDNA by first digesting it with ClaI and BamHI, purifying it, and then mixing it with the EcoRV/BamHI fragment of pcD-125 in a standard ligation solution containing 0.1 micromolar of the following synthetic linker:

```
TCG ATG CAC AAG TGC GAT         SEQ. ID NO. 7
    AC GTG TTC ACG CTA          SEQ. ID NO. 8
```

The insert-containing vector was selected as described above and propagated in E. coli K-12 strain JM101. IL-4 was extracted as follows. JM101 cells were sonicated in their culture medium and centrifuged. The pellet was resuspended in 4 M guanidine and 2 mM dithiothreitol, and again centrifuged. The supernatant was tested for biological activity and found to exhibit TCGF activity comparable to that of supernatants of pcD-125-transfected COS7 cells.

Example 3.

Expression of Native Human IL-4 and Muteins $\Delta^{1-4}$ and $IS^O$(Gly-Asn-Phe-Val-His-Gly) in *Saccharomyces cerevisiae*

Native human IL-4 cDNA and two mutants thereof were cloned into the plasmid pMF-alpha8 and expressed in the yeast *Saccharomyces cerevisiae*. The construction and application of pMF-alpha8 for expressing non-yeast proteins is described fully in Miyajima et al, *Gene*, Vol. 37, pp. 155-161 (1985); and Miyajima et al, *EMBO Journal*, Vol. 5, pp. 1193-1197 (1986). pMF-alpha8 is deposited with the American Type Culture Collection (Rockville, Md.) under accession number 40140.

A. Human IL-4 Mutein $\Delta^{1-4}$

Plasmid pcD-125 was isolated and digested with EcoRV and BamHI. The EcoRV/BamHI fragment containing the human IL-4 cDNA was isolated, treated with DNA polymerase I (Klenow fragment) to fill in the BamHI cut, and kinased (i.e. phosphorylated). pMF-alpha8 was digested with StuI and combined with the kinased EcoRV/BamHI fragment of pcD-125 in a standard ligation solution to form plasmid phIL-4-2. phIL-4-2 was used to transform S. cerevisiae 20B-12 (MATalpha trp1-289 pep4-3), which was obtained from the Yeast Genetic Stock Center, University of California, Berkeley. Yeast cells were grown in synthetic medium containing 0.67% Yeast Nitrogen Base without amino acids, 2% glucose, and 0.5% Casamino acids (Difco). The yeast cells were transformed with the plasmids by the lithium acetate method of Ito et al, *J. Bacteriol.*, Vol. 153, pp. 163-168 (1983), and transformants were selected in synthetic medium lacking tryptophan. Supernatant of a transformant culture was tested for TCGF activity.

B. Human IL-4 Mutein $IS^O$(Gly-Asn-Phe-Val-His-Gly) SEQ. ID NO. 12.

The pMF-alpha8 insert for expression of mutein $IL^O$(Gly-Asn-Phe-Val-His-Gly SEQ. ID NO. 12) was prepared exactly as for mutein $\Delta^{1-4}$, except that the NaeI/BamHI fragment from pcD-125 was used. The resulting plasmid was designated phIL-4-1. Several dilutions of supernatant from phIL-4-1-transformed yeast cells were tested for TCGF activity. The supernatants were also tested for BCGF activity on both anti-IgM and SAC-activated B lymphocytes. The assays were performed as described above, and the results are given in Table IV.

TABLE IV

| | BCGF Activity of Supernatants of phIL-4-3 Transformed Yeast Cells | |
|---|---|---|
| | [$^3$H]—Thymidine Incorporation (cpm) | |
| % (vol/vol) of supernatants added | SAC-activated B Lymphocytes | Anti-IgM Beat Activated B Lymphocytes |
| .0 | 3633 ± 1239 | 641 ± 69 |
| 0.09 | 7610 ± 310 | 13221 ± 472 |
| 0.19 | 9235 ± 181 | — |
| 0.39 | 10639 ± 786 | 16681 ± 310 |
| 0.78 | 10372 ± 572 | 18090 ± 1248 |
| 1.56 | 9905 ± 328 | 17631 ± 1216 |
| 3.12 | 11354 ± 836 | 18766 ± 1179 |
| 6.25 | 10481 ± 541 | 19810 ± 1349 |
| 12.5 | 9641 ± 30 | 18136 ± 1126 |
| 25. | 8253 ± 857 | 14750 ± 1125 |

C. Expression of Native Human IL-4 in Yeast.

cDNA coding for native human IL-4 was cloned into pMF-alpha8 by first inserting bases upstream of the N-terminal His codon to form a KpnI restriction site. After cleavage by KpnI and treatment by DNA polymerase I, the blunt-ended IL-4 cDNA was inserted into the StuI site of pMF-alpha8. The KpnI site was formed by use of standard site-specific mutagenesis. Briefly, pcD-125 was digested with BamHI, and the fragment containing the entire human IL-4 cDNA was isolated and inserted into the BamHI site of M13mp8. Single-stranded M13mp8 containing the insert was isolated and hybridized to the following synthetic oligonucleotide which served as a primer:

```
5'-TCCACGGA GGTAC  CACAAGTG-3'         SEQ. ID NO. 9
```

The inserted nucleotides are boxed. The plasmid containing the mutated IL-4 cDNA was identified by an oligonucleotide probe, propagated, isolated, and treated with KpnI and BamHI. The KpnI/BamHI fragment was isolated, treated with DNA polymerase I (Klenow fragment) to generate blunt ends, kinased, and ligated with StuI-digested pMF-alpha8. Yeast was transformed by the resulting pMF-alpha8 plasmids, designated phIL-4-3, as described above, and supernatants were tested for TCGF activity. The supernatants displayed TCGF activity comparable to that observed for supernatants of phIL-4-1-transformed yeast.

Example 4

Construction and Expression of Human IL-4 Mutein Ile[52] in *E. coli*.

Leu at position 52 (relative to the N-terminus of the native human IL-4) is changed to Ile to form human IL-4 mutein Ile[52]. The pUC18 plasmid of Example VII of WO 87/02990 containing the synthetic human IL-4 gene of FIG. 6A (of aforementioned WO'990) is digested with PstI and MluI and purified. The above purified pUC18 is mixed with the synthetic double-stranded fragment illustrated below and ligated. The altered part of the base sequence is boxed. The resulting puC18 is transfected into *E. coli* K-12 strain JM101, or the like, and expressed.

```
GA GCT GCT ACC GTT  ATC  CGT      SEQ. ID NO. 10
ACG TCT CGA CGA TGG CAA  TAG  GCA

CAG TTC TAC TCT CAC CAC GAA AAA
GTC AAG ATG AGA GTG GTG CTT TTT
GA A
CTG TGC GC                         SEQ. ID NO. 11
```

PstI/MluI Replacement Fragment For Generating Human IL-4 Mutein Ile[52]

After culturing, protein is extracted from the JM101 cells using standard techniques, and dilutions of the extracts are tested for biological activity.

---

We claim:

1. A method of stimulating the formation of bone in a human patient, comprising administering to a human patient bone stimulating effective amounts of substances selected from the group consisting of (1) recovered and purified human interleukin 4, (2) a substance wherein amino acids of the peptide structure of human interleukin 4 are subjected to sugar addition, (3) recombinant human interleukin 4, and (4) an analogue of human interleukin 4 wherein amino acids of the polypeptide structure of human interleukin 4 are replaced with amino acids such that the analogue exhibits bone stimulating activity.

2. The method according to claim 1, wherein the active ingredient is recombinant human interleukin 4.

3. A method of stimulating the formation of osteoblasts, comprising administering to a human patient bone stimulating effective amounts of substances selected from the group consisting of (1) recovered and purified human interleukin 4, (2) a substance wherein amino acids of the peptide structure of human interleukin 4 are subjected to sugar addition, (3) recombinant human interleukin-4, and (4) an analogue of human interleukin 4 wherein amino acids of the polypeptide structure of human interleukin 4 are replaced with amino acids such that the analogue exhibits bone stimulating activity.

4. The method according to claim 3, wherein the active ingredient is recombinant human interleukin 4.

5. A method of stimulating the formation of bone in a human patient, comprising administering to a human patient bone stimulating effective amounts of substances selected from the group consisting of (1) recovered and purified natural human interleukin 4, (2) a substance having the polypeptide structure of natural human interleukin 4 wherein amino acids of the polypeptide structure are subjected to sugar addition; and (3) recombinant human interleukin 4.

6. A method of stimulating the formation of osteoblasts, comprising administering to a human patient bone stimulating effective amounts of substances selected from the group consisting of (1) recovered and purified natural human interleukin 4, (2) a substance having the polypeptide structure of natural human interleukin 4 wherein amino acids of the polypeptide structure are subjected to sugar addition; and (3) recombinant human interleukin 4.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 129 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:1:

```
His Lys Cys Asp Ile Thr Leu Gln Glu Ile Ile Lys Thr Leu Asn Ser
 1               5                  10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:2:

AATTCCACAA GTGCGAT      17

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:3:

ATCGCACTTG TGG      13

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:4:

GGAATTCAGA AGCTTGCGGC TAC      23

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:5:

AGCTCACAAG TGCGAT      16

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:6:

ATCGCACTTG TG      12

( 2 ) INFORMATION FOR SEQ ID NO:7:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (iii) HYPOTHETICAL: NO (xi) SEQUENCE DESCRIPTION: SEQ ID NO:7:

TCGATGCACA AGTGCGAT                                                    18

(2) INFORMATION FOR SEQ ID NO:8:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (iii) HYPOTHETICAL: NO (xi) SEQUENCE DESCRIPTION: SEQ ID NO:8:

ATCGCACTTG TGCA                                                        14

(2) INFORMATION FOR SEQ ID NO:9:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (iii) HYPOTHETICAL: NO (xi) SEQUENCE DESCRIPTION: SEQ ID NO:9:

TCCACGGAGG TACCACAAGT G                                                21

(2) INFORMATION FOR SEQ ID NO:10:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (iii) HYPOTHETICAL: NO (xi) SEQUENCE DESCRIPTION: SEQ ID NO:10:

GAGCTGCTAC CGTTATCCGT CAGTTCTACT CTCACCACGA AAAAGACA                   48

(2) INFORMATION FOR SEQ ID NO:11:

(i) SEQUENCE CHARACTERISTICS:
      (A) LENGTH: 56 base pairs
      (B) TYPE: nucleic acid
      (C) STRANDEDNESS: single
      (D) TOPOLOGY: linear (iii) HYPOTHETICAL: NO (xi) SEQUENCE DESCRIPTION: SEQ ID NO:11:

CGCGTGTCTT TTTCGTGGTG AGAGTAGAAC TGACGGATAA CGGTAGCAGC TCTGCA          56

(2) INFORMATION FOR SEQ ID NO:12:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

```
Gly  Asn  Phe  Val  His  Gly
 1                  5
```